(12) United States Patent
Westenskow et al.

(10) Patent No.: US 7,774,060 B2
(45) Date of Patent: Aug. 10, 2010

(54) SYSTEM FOR PROVIDING EMERGENCY MEDICAL CARE WITH REAL-TIME INSTRUCTIONS AND ASSOCIATED METHODS

(75) Inventors: Dwayne R. Westenskow, Salt Lake City, UT (US); Joseph A. Orr, Park City, UT (US); Noah Syroid, Salt Lake City, UT (US); Daniel Snell, Tucson, AZ (US); James Agutter, Salt Lake City, UT (US); Frank Drews, Salt Lake City, UT (US); Srinath Lingutla, Salt Lake City, UT (US); Santosh Balakrishnan, Salt Lake City, UT (US); Kai Kuck, Hamburg (DE); Lara Brewer, Bountiful, UT (US)

(73) Assignees: University of Utah Research Foundation, Salt Lake City, UT (US); Axon Medical, Inc., Park City, UT (US)

(*) Notice: Subject to any disclaimer, the term of this patent is extended or adjusted under 35 U.S.C. 154(b) by 0 days.

(21) Appl. No.: 11/157,218

(22) Filed: Jun. 20, 2005

(65) Prior Publication Data

US 2006/0111749 A1    May 25, 2006

Related U.S. Application Data

(63) Continuation of application No. PCT/US03/40834, filed on Dec. 22, 2003.

(60) Provisional application No. 60/435,907, filed on Dec. 20, 2002.

(51) Int. Cl.
*A61N 1/39* (2006.01)
(52) U.S. Cl. ........................................................ 607/5
(58) Field of Classification Search ................ 607/3–8; 601/41–44; 600/523
See application file for complete search history.

(56) References Cited

U.S. PATENT DOCUMENTS

| | | | |
|---|---|---|---|
| 5,782,878 A * | 7/1998 | Morgan et al. | 607/5 |
| 6,334,070 B1 * | 12/2001 | Nova et al. | 607/5 |
| 6,351,671 B1 * | 2/2002 | Myklebust et al. | 607/5 |
| 6,356,785 B1 * | 3/2002 | Snyder et al. | 607/5 |

FOREIGN PATENT DOCUMENTS

| | | | |
|---|---|---|---|
| WO | WO 99/24114 | * | 5/1999 |
| WO | WO 00/30712 | * | 6/2000 |
| WO | WO 03/105720 | * | 12/2003 |
| WO | WO 03/105720 A2 | * | 12/2003 |

* cited by examiner

OTHER PUBLICATIONS

Wik et al. "An automated voice advisory manikin system for training in basic life support without an instructor. A novel approach to CPR training," Resuscitation 50 (2001) 167-172.*

*Primary Examiner*—Mark W Bockelman
*Assistant Examiner*—Eric D. Bertram
(74) *Attorney, Agent, or Firm*—Thorpe North & Western LLP

(57) ABSTRACT

A basic life support system (BLSS) includes a processing element and an output element, such as a display screen or an audio output element, for providing an individual with real-time instructions on providing emergency medical care to a patient until paramedics or other healthcare professionals arrive to take over care for the patient. The instructions may be provided as graphics, including animations, as text, audibly, or as a combination of visible and audible elements. The BLSS may be configured for providing emergency medical care to individuals who have suffered from ventricular fibrillation. Accordingly, the BLSS may also include a defibrillation apparatus, an air or oxygen supply, a respiratory interface, one or more sensors, or a combination thereof.

31 Claims, 8 Drawing Sheets

SYSTEM FOR PROVIDING EMERGENCY MEDICAL CARE WITH REAL-TIME INSTRUCTIONS AND ASSOCIATED METHODS

CROSS-REFERENCE TO RELATED APPLICATIONS

This application is a continuation of PCT International Application No. PCT/US2003/040834, filed Dec. 22, 2003, designating the United States of America, and published, in English, as PCT International Publication No. WO 2004/058351 A1 on Jul. 15, 2004, which application claims priority to U.S. Provisional Application No. 60/435,907, filed Dec. 20, 2002, the entire contents of each of which are hereby incorporated herein by this reference.

GOVERNMENT INTEREST

This invention was made with government support under Grant #NAS 9-03047 awarded by the National Aeronautics and Space Administration. The government has certain rights to this invention.

TECHNICAL FIELD

The present invention relates to apparatus and systems for assisting responding individuals, or responders, in providing emergency medical care to others. In particular, the present invention relates to emergency medical care apparatus and systems that provide graphic displays to instruct responders on the appropriate manner in which emergency medical care should be given. More specifically, the present invention relates to apparatus and systems for instructing responders, in real time, on how to provide respiratory or cardiopulmonary resuscitation.

BACKGROUND OF RELATED ART

Sudden cardiac arrest resulting from heart attack, or cardiac arrest or ventricular fibrillation (VF), a spontaneous, mostly fatal interruption of normal heartbeat, is a leading cause of death. Survival rates for VF are about 5 to 10 percent.

Sometimes the stricken individual, or VF victim or "patient," will be fortunate enough to suffer from VF in proximity to someone who has received cardiopulmonary resuscitation (CPR) training. Nonetheless, a large number of CPR-trained individuals are not able to provide effective emergency care when an individual has suffered from VF. In this regard, Brennan and Braslow found that 45% of 226 recent graduates of CPR training failed to open the airway prior to checking for respiration and that 50% of the recent graduates failed to adequately assess the patient's respiratory status. Failure in these critical CPR administration skills may contribute to poor survival rate following out-of-hospital VF.

Even when CPR has been properly administered to an individual who has suffered VF, survival rates decrease by about 10 percent for every minute that goes by without a stricken individual receiving a defibrillation shock. In the United States, it generally takes about six to twelve minutes for the average emergency medical services (EMS) team to arrive at the scene of a medical emergency.

Automatic external defibrillators (AED) can significantly increase successful outcomes following sudden cardiac arrest. Success rates rise from 3% to 70% when AEDs are used within 3-4 minutes of arrest, with recent studies showing that up to 70 percent of VF victims survive when AEDs are accessible. Clearly, early defibrillation is the key to saving lives.

Conventionally, use of AEDs to treat VF has been limited to caregivers with some level of medical expertise, including, without limitation, doctors, nurses, emergency medical technicians (EMTs), law enforcement personnel, fire personnel, security guards, health club employees, flight attendants, lifeguards, and office managers. The American Heart Association (AHA) estimates that, in the U.S., nearly 120,000 of the approximately 300,000 people who die annually from sudden cardiac arrest could be saved with public access defibrillation. According to the AHA, "Public access defibrillation, which places AEDs in the hands of trained laypersons, has the potential to be the single greatest advance in the treatment of VF cardiac arrest since the development of CPR." Only recently, however, have public access AEDs become available.

In view of the foregoing, the federal government of the U.S. has taken several measures to reduce the incidence of deaths that are attributable to out-of-hospital occurrences of VF. For example, the U.S. Occupational Safety and Health Administration (OSHA) has endorsed the placement of AEDs in the workplace, the U.S. Congress has passed the Community Access to Early Defibrillation Act to provide funds for the purchase of defibrillators, and the U.S. Congress has enacted the 1999 Cardiac Arrest Survival Act, which mandates placement of defibrillators in all federal buildings.

Although efforts are being made to place AEDs in a variety of locations, currently available AEDs are difficult for untrained or minimally trained individuals to use. For example, members of the flight crew on the International Space Station (ISS) are only required to have 40 hours of emergency medical training. Upon discovering a "patient in distress," two members of the flight crew onboard the ISS are responsible for stabilizing the injured crew member until support can be provided by ground-based flight surgeons. When the ISS is not in communication with ground-based support (the link with ground-based flight surgeons is only useful about half of the time and is subject to blackout periods that last for about ten or fifteen minutes), the crew is trained to use the Integrated Medical Group (IMG) Medical Checklist and follow a twenty-four page Advanced Cardiac Life Support algorithm. This is a formidable task for crewmembers with only 40 hours of medical training.

Recent studies indicate that the treatment of a VF victim following the current National Aeronautics and Space Administration (NASA) protocol would take too long, primarily due to the lengthy text-based instructions and difficulty in understanding such instructions in a high-stress situation.

Accordingly, there is a need for apparatus, systems, and methods for providing responders, including untrained and minimally trained individuals, with emergency medical care instructions, including, but not limited to, administration of CPR and effective use of AED, in real time.

DISCLOSURE OF INVENTION

The present invention includes apparatus and systems by which emergency medical treatment may be provided and for providing a responder with instructions on administering such emergency medical care.

In one embodiment, an apparatus according to the present invention comprises a Basic Life Support System (BLSS) configured for use in treating VF patients. Such an apparatus includes, among other things, a power supply, AED pads, and at least one visual display element for providing graphic instructions on use of the AED pads. Additionally, an apparatus according to the present invention may include an air or oxygen supply, means for facilitating introduction of the air or oxygen into the lungs of the patient, referred to herein as a "respiratory interface," one or more sensors (e.g., for monitoring one or more of the patient's respiration, blood oxygen level, pulse, heart, etc.), or a combination of any of the foregoing.

Graphic instructions according to the present invention are designed to optimize (i.e., minimize) the amount of time it takes a responder who is administering emergency medical care to correctly perform certain functions. In order to avoid confusing the responder, the graphic instructions may provide accurate depictions of other components of the apparatus or system. The graphic instructions may be accompanied by or supplemented with text instructions, audible instructions or alarms, appropriately positioned symbols, and the like.

Examples of the instructions that may be provided to guide a responder through CPR procedures and the use of an AED include providing graphic instructions on appropriate head tilt, chin lift, and jaw thrust to maintain a patent airway, showing a responder how to place and seal a mask or other breathing element in communication with the patient's airway and how to provide air or oxygen to the lungs of the patient, and illustrating proper placement and use of the AED pads.

An apparatus or system according to the present invention may also include one or more processing elements, such as a central processing unit, which may monitor the patient, monitor operation of the apparatus or system, or provide the responder with instructions, which instructions may (or may not) be based on feedback provided by sensors of the apparatus or system, the responder, or another individual.

Apparatus for use in providing instructions and support in treating other medical emergencies are also within the scope of the present invention.

Other features and advantages of the present invention will become apparent to those of ordinary skill in the art through consideration of the ensuing description, the accompanying drawings, and the appended claims.

BRIEF DESCRIPTION OF THE DRAWINGS

In the drawings, which depict various aspects of exemplary embodiments of the present invention.

DETAILED DESCRIPTION OF THE INVENTION

Basic Life Support System

Figure 1:
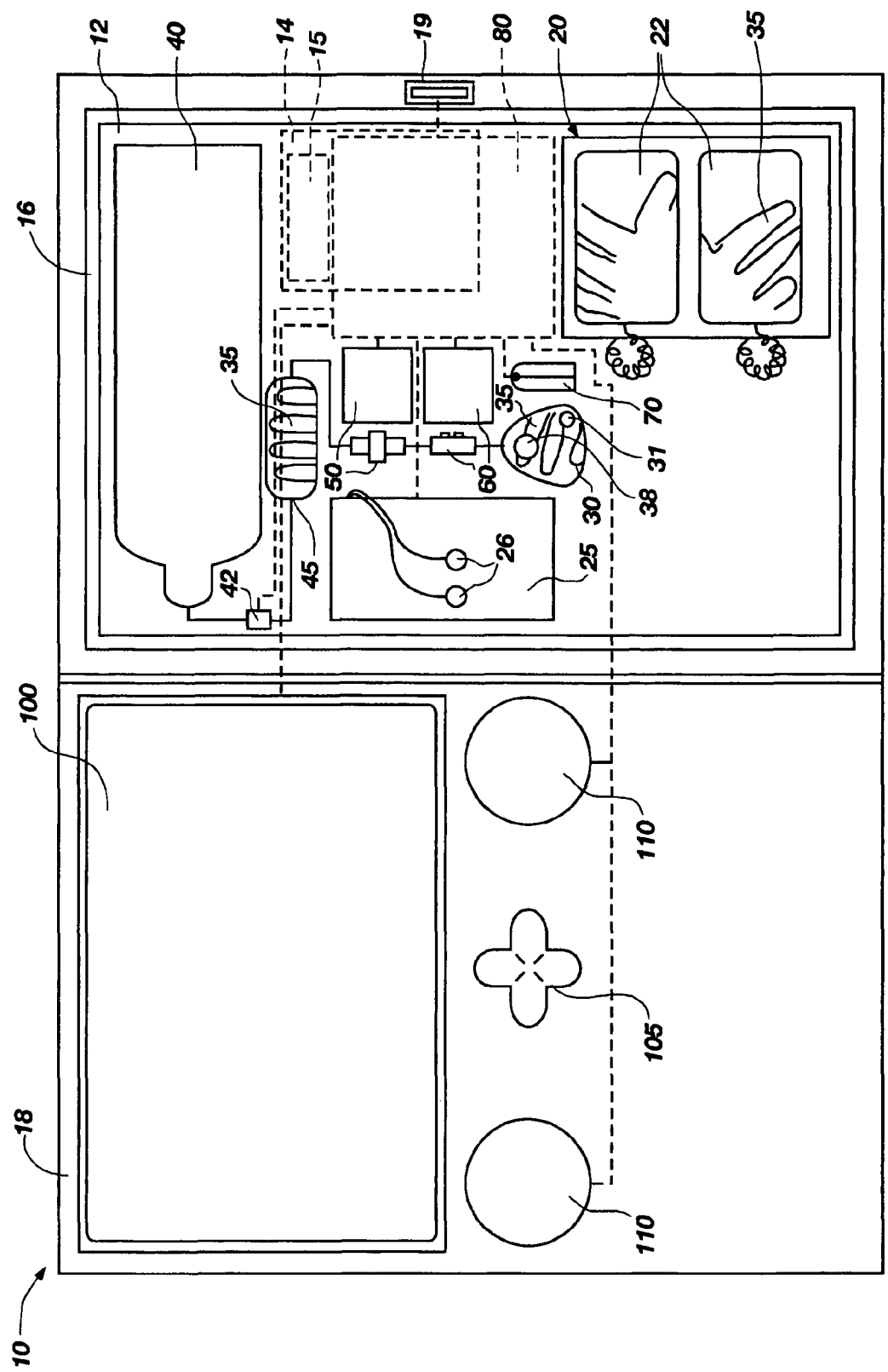
FIG. 1 is a schematic representation of a BLSS according to the present invention.

An exemplary embodiment of a BLSS 10 that incorporates teachings of the present invention is shown in FIG. 1. BLSS 10 includes a chassis 12 which carries a power supply 14 and other elements of BLSS 10, as well as an enclosure 16 within which the other elements of BLSS 10 are contained. Examples of other elements that may be included in BLSS 10 include, without limitation, an AED 20, a respiratory interface 30 (e.g., the depicted mask), a responder-protection filter 38, an air or oxygen supply 40, and sensors 25, 50, 60, 70 for respiratory or cardiovascular support. Additionally, the illustrated BLSS 10 includes a processing element 80 and a display screen 100 in communication with processing element 80 for conveying instructions with text and graphics, as well as an input element 105 for selecting from options provided on display screen 100 and inputting other information. BLSS 10 may also include an audio output element 110 associated with processing element 80.

BLSS 10 may also include any of a variety of other elements that are useful for providing functions that are well-known in the art but, for the sake of simplicity, are not described in detail herein. For example, BLSS 10 may include blood pressure monitoring apparatus, rebreathing apparatus, or $CO_2$ absorbers to optimize the efficiency with which BLSS 10 uses oxygen-rich gas.

As it may be desirable to impart BLSS 10 with some degree of portability, the overall system may consume a relatively small amount of power, have a relatively low weight, and be relatively inexpensive.

BLSS 10 may be configured to identify the functions and proper use of the various components thereof, include components which are simply and intuitively used by a responder, and minimize the mental workload on a responder, thereby preventing errors by the responder and aiding the responder in providing quality emergency medical care to a patient, regardless of the responder's level of expertise in providing such care.

Power supply 14 may comprise any type of power supply suitable for providing the power necessary to operate the various elements of BLSS. Power supply 14 may be configured to be connected to a power source (i.e., "plugged in") or include a battery 15 to provide true portability.

Enclosure 16, within which chassis 12 and other elements of BLSS 10 are contained, includes a door 18, by which ready access to the various elements of BLSS 10 may be obtained. Door 18 may be associated with a switch 19, as known in the art, to automatically provide power other elements of BLSS 10 (e.g., processing element 80, AED 20, sensors 25, 50, 60, 70, etc.) as door 18 is opened.

AED 20 comprises a defibrillation apparatus of any suitable known type. Among other known components, AED 20 includes defibrillation pads, or simply "pads" 22, that are configured to contact the chest of a patient, as known in the art, and to electrically shock the patient, also as known in the art.

Each of respiratory interface 30, responder-protection filter 38, air or oxygen supply 40, delivery component 45, and sensors 25, 50, 60, 70 may also be referred to as a "respiratory support apparatus," as each of these elements is configured to support the provision of respiratory support to a patient.

Respiratory interface 30 is configured to form an airtight seal with the mouth, nose, or both, of a patient to establish reliable flow communication with the airway (e.g., trachea and lungs) of the patient. Respiratory interface 30 may optionally include a pressure sensor 31, which provides an indication of the amount of pressure applied to respiratory interface 30. Such a pressure sensor 31 may communicate with processing element 80 of BLSS 10 or another processing element (not shown), which may, in turn, be configured to output information about the amount of pressure being applied to respiratory interface 30. Pressure sensors 31 are particularly useful for use in warning a responder that too little or too much pressure is being applied to respiratory interface 30 embodiments (e.g., masks, breathing tubes with protective covers, etc.) that cover a portion of the face and that require the responder to apply pressure to ensure that an adequate seal has been established and maintained.

Figure 2:
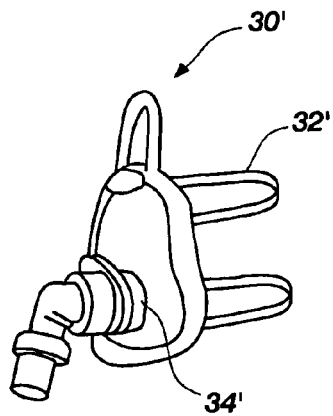
FIGS. 2 through 7 depict various examples of respiratory interfaces that may be used with a BLSS of the present invention.
Figure 4:
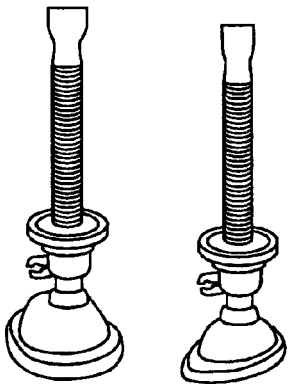
Figure 3:
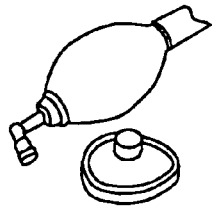

FIG. 2 illustrates a respiratory interface that comprises a mask 30'. Mask 30' has a configuration which permits a responder to intuitively place it properly on the face of a patient. Mask 30' may also be configured to seal effectively on most shapes and sizes of faces. One or more straps 32' on mask 30' may facilitate retention thereof on the face of the patient and maintenance of an adequate seal. Further, mask 30' may be configured for comfort. Additionally, mask 30' may include a mouthpiece 34' or other means therein to help maintain an open airway.

The deadspace within mask 30' may be configured to facilitate accurate etCO$_2$ detection and to optimize the amount of ventilation for each breath delivered to the patient (e.g., about 30 mL or less). Mask 30' may also be configured to minimize airway resistance so as to minimize the work of breathing required by both BLSS 10 and the patient.

Mask 30' may, by way of example only, comprise a continuous-positive-airway-pressure (CPAP) mask of known type, available from a variety of manufacturers, including Respironics, Inc., of Murraysville, Pa.

Figure 6:
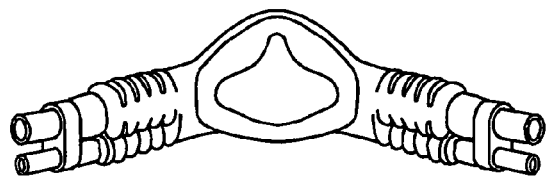
Figure 5:
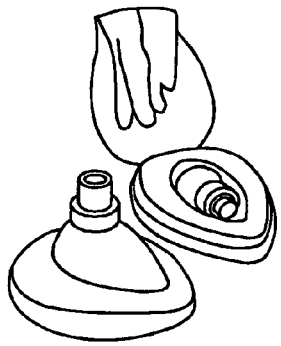

Alternatively, as shown in FIGS. 3 through 6, mask 30' may comprise the mask portion of a bag-valve-mask (BVM) resuscitator (FIG. 3), a non-bag BVM system (FIG. 4), a resuscitation mask (e.g., the RONDEX PRM mask available from Rondex Products, Inc. of Rockford, Ill., which is designed for use by lifeguards, public safety personnel, and rescue personnel) (FIG. 5), a low-profile scavenger mask insert (e.g., that available from Porter Instrument Company, Inc., of Hatfield, Pa., which contains a disposable insert and is often used for nitrous oxide delivery and monitoring respiration while scavenging volatile anesthetics and monitoring CO$_2$ (FIG. 6).

A good seal between mask 30' and the face of a patient may be achieved and maintained by use of a suitable adhesive material.

Figure 7:
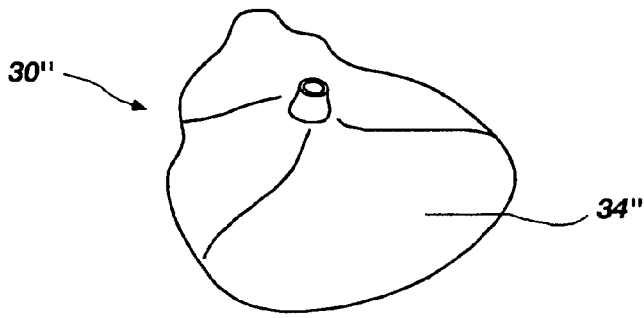

Another example of a respiratory interface that may be included in a BLSS 10 according to the present invention is the mouthpiece 30" shown in FIG. 7. Mouthpiece 30", which was originally designed to provide protection during mouth-to-mouth resuscitation, includes a face shield 34". An adhesive may be applied to a surface of face shield 34" and may be covered with a removable film until use of mouthpiece 30" is required. The combination of face shield 34" and adhesive thereon provides an easy-to-place patient interface which seals easily and well to the face of a patient. Face shield 34" may be formed from a transparent or semi-transparent material, which facilitates visual monitoring of the status of the patient.

Air or oxygen supply 40 may be included as a part of BLSS 10 to increase the fraction of oxygen provided to and inspired by the patient. Air or oxygen supply 40 may, by way of nonlimiting example, comprise a conventional oxygen cylinder. To prevent hypoxia, which may lead to anaerobic metabolism and metabolic acidosis and can blunt the beneficial effects of chemical and electric therapy, air or oxygen supply 40 may comprise substantially pure oxygen or a gas mixture including higher than normal (i.e., greater than about 20%) oxygen. It is currently preferred that air or oxygen supply 40 be portable, such as a four inch tall oxygen cylinder, which weighs 1.95 lbs. and can provide 33 L of oxygen at sea level atmospheric pressure, which is equivalent to a 15 minute supply of oxygen at a delivery rate of about 2.2 L/min. These cylinders are commercially available from Aeromedix.com LLC of Jackson Hole, Wyo.

Optionally, if air or oxygen supply 40 is a gas tank, it may be equipped with a fill meter 42 of a known type. Fill meter 42 indicates the amount of gases (volume, estimated duration, etc.) that remain within the gas tank. Such information may be displayed directly by fill meter 42, by display screen 100 (e.g., by way of signals transmitted to and from processing element 80), or by a combination thereof.

Communication between air or oxygen supply 40 and respiratory interface 30 may be established by known processes and with known apparatus, referred to herein as "delivery components" 45. For example, if respiratory interface 30 comprises a BVM resuscitator, delivery component 45 may comprise the bag of the BVM resuscitator, as well as inlets, valves, and flexible reservoir tubing deliver thereof, which are collectively configured to deliver a relatively large tidal volume of oxygen-enriched air to the patient when the bag of the BVM resuscitator is squeezed.

As another example, in a non-bag BVM system, the lungs of a responder, rather than a bag, deliver a tidal volume of oxygen-rich gases from air or oxygen supply 40 to the patient through the mask (i.e., respiratory interface 30) thereof. Thus, the valve of a non-bag BVM system and tubing between air or oxygen supply 40 and respiratory interface 30 comprise a delivery component 45. Additionally, the tubing of such a delivery component 45 acts as a reservoir to increase the amount of oxygen delivered to the patient with each inspiratory breath.

With returned reference to FIG. 1, responder-protection filter 38 may be included in BLSS 10 when BLSS 10 is configured to have the responder deliver air to the lungs of the patient (e.g., by a somewhat protected version of mouth-to-mouth, with respiratory interface 30 being located between the mouth of the patient and the mouth of the responder). Responder-protection filter 38 may be positioned so as to prevent passage of pathogens between the patient and the responder (e.g., within respiratory interface 30 or at or near an end thereof) and, thereby, providing some degree of protection to both the patient and the responder. Accordingly, responder-protection filter 38 may comprise any filtration material or materials and, optionally, antimicrobial materials, that are suitable for this purpose.

Sensor 25 includes a portable electrocardiogram of a known type and, accordingly, is also referred to herein as "electrocardiogram 25." Electrocardiogram 25 includes electrodes 26, which are configured to be secured at appropriate locations on the chest of a patient to monitor activity of the patient's heart, as known in the art. In addition to monitoring the patient's heart, electrocardiogram 25 may monitor chest movements that are caused by respiration of the patient.

Sensors 50, 60, 70 of BLSS 10, which may, more specifically, comprise a gas analyzer 50 (e.g., a carbon dioxide or oxygen analyzer), a flow meter 60, and a pulse oximeter 70 (which measures the level of oxygen in the blood of the patient, or "blood oxygen saturation") may monitor the respiratory activity of the patient, whether the patient is adequately ventilated, or both.

Additionally, sensors 25, 50, 60, 70 may communicate data (in the form of electronic signals) directly or indirectly to processing element 80 that, in accordance with programming of processing element 80, may be used to provide the responder with information about the status of patient and BLSS 10, as well as guide the responder while emergency medical care, in the form of respiratory or cardiovascular support, is being provided to a patient.

By way of example only, sensors 25, 50, 60, 70 may be used, as known in the art, to monitor the patient's airway resistance, to monitor tidal volumes, to detect spontaneous breathing, to assess adequacy of alveolar ventilation, and monitor $CO_2$ production ($VCO_2$) end-tidal $CO_2$ ($etCO_2$) concentrations. As a more specific example, respiratory signals obtained with electrocardiogram 25 may be used, as known in the art, to distinguish between efforts in ventilating the patient or spontaneous breathing by the patient, and the actual volumes of respiratory gases that move into and out of the patient's lungs, which may provide an indication of the effectiveness of the volumes of ventilatory gases that are provided to the patient (e.g., an indication of whether any leaks or obstructions are present in the airway).

Accordingly, upon receiving and evaluating signals from one or more of sensors 25, 50, 60, 70, processing element 80 may respectively instruct the responder to check for obstructions in the airway and make sure the patient's airway is open, advise the responder if mask leaks are present, assess the effectiveness of chest compressions provided by the responder, direct the responder to give breaths when needed, assist the responder maintaining both an adequate breathing rate and large enough tidal volumes to maintain $SaO_2$, and direct the responder on when CPR breaths are to be provided to the patient, optimizing the trade-offs between alveolar ventilation, prevention of barotraumas, and use of oxygen.

The respiratory monitor available from Respironics, Inc., under the trademark $CO_2$SMO PLUS!® is configured to monitor both carbon dioxide in the respiration of a patient, as well as the flow of the patient's respiration. Accordingly, the $CO_2$SMO PLUS!® may be used as gas analyzer 50 and flow meter 60 (with a respective gas sensor and flow sensor) of a BLSS 10 that incorporates teachings of the present invention to monitor airway pressure, flow, and mainstream $CO_2$ concentration of the patient's respiration. Additionally the $CO_2$SMO PLUS!® is configured to have a pulse oximeter 70 operatively coupled thereto to facilitate monitoring of the oxygen saturation of the patient's arterial blood ($SaO_2$). As various components of the $CO_2$SMO PLUS!® communicate with and, thus, share data with one another, a variety of blood and respiratory parameters, including the presence of obstructions (i.e., resistance) and leaks in an airway, may be calculated by a processing element of the $CO_2$SMO PLUS!® Additionally, at least one processing element of the $CO_2$SMO PLUS!® and communication port associated therewith facilitate the communication of data (embodied as electronic signals) to another computer, such as processing element 80 of BLSS 10.

Of course, BLSSs 10 that include a gas analyzer 50, a flow meter 60, and pulse oximeter 70 that are separate from one another are also within the scope of the present invention. Each of these components may comprise a known apparatus, each of which is available from, among a variety of sources, Respironics, Inc.

Cheaper alternatives with sufficient accuracy are also within the scope of the present invention. For example, gas analyzer 50 may comprise a so-called colorimetric $CO_2$ sensor, such as the sulfonephthalein based pH-sensitive chemical sensor available from ICOR AB of Bromma, Sweden. Such a gas analyzer 50 includes an element which changes color when exposed to $CO_2$-containing expiratory gases. For example, a change in color from purple to yellow allows a rough estimation of the amount of $CO_2$ in a patient's respiration. The response is sufficiently rapid to allow breath-to-breath $CO_2$ monitoring.

Figure 8:
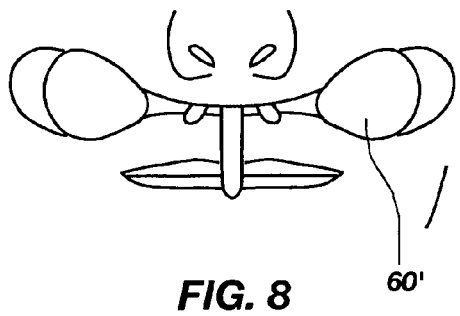
FIGS. 8 and 9 show examples of flow meters that may be used in a BLSS that incorporates teachings of the present invention.

Thermistor sensors 60', an example of which is shown in FIG. 8, comprise an example of a simple and inexpensive flow meter 60. When placed at or near the nose or mouth, thermistor sensors 60' are capable of providing signals that are indicative of respiratory airflow. Although they are less quantitative than more expensive, complex flow meters, thermistor sensors may reliably detect spontaneous breathing during CPR. An exemplary thermistor-type flow meter is available from S.L.P Scientific Laboratory Products, Ltd., of Tel-Aviv, Israel, and combines an oral thermistor and two nasal thermistors with a processor and display in a self-contained low-cost sensor strip. Such a device could, by way of example only, be mounted within a mask 30' (FIGS. 2 through 6) and automatically activated when mask 30' is placed upon the face of a patient.

Figure 9:
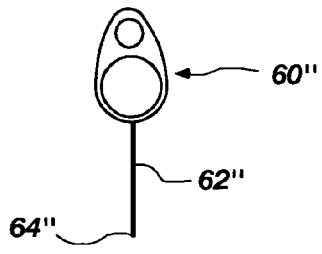

Another example of flow meter 60 that may be used in a BLSS according to the present invention is a fiber optic humidity-based respiratory monitor 60", an example of which is shown in FIG. 9. Basically, the tip 64" of a thin optical fiber 62" monitors the condensation and evaporation cycles that occur with respiration. Due to their small size, they may be incorporated into any type of respiratory interface 30. Like thermistor-type flow meters, fiber optic humidity based respiratory monitors reliably detect breathing.

Pulse oximeter 70 may comprise any suitable pulse oximetry sensor and monitor. By way of example only, when the $CO_2$SMO PLUS!® is employed as a part of gas analyzer 50 and flow meter 60, pulse oximeter 70 may comprise any of the pulse oximetry sensors available from Respironics, Inc., that are compatible therewith.

Processing element 80 of BLSS 10 is configured to implement a treatment algorithm of the present invention. In so doing, processing element 80 may be configured (e.g., by way of communication ports or other communication apparatus) to communicate with other elements of BLSS 10, including, but not limited to sensors 25, 50, 60, and 70. Processing element 80 outputs instructions and, optionally, information, to display screen 100, providing ready access to such instructions by a responder. Additionally, processing element 80 may communicate with and control operation of AED 20, flow of oxygen-rich gases from air or oxygen supply 40, or both.

Processing element 80 may also be configured to maintain a record of use, including data measured during use thereof, instructions and alarms or warnings provided, and the time at which each recorded event occurred. Additionally, records of pertaining to maintenance activities, such as recharging a battery of power supply 14, refilling air or oxygen supply 40 if air or oxygen supply 40 comprises a tank, replacement, maintenance, or cleaning of other elements of BLSS, or the like, may be recorded and maintained by processing element 80.

Figure 10:
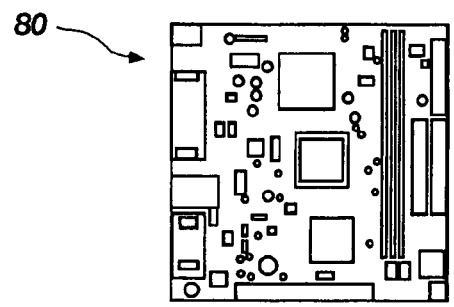
FIG. 10 shows an exemplary processing element of a BLSS according to the present invention.

As a nonlimiting example, processing element may comprise a central processing unit (CPU) of a known type. The CPU may comprise a single-board CPU (SBC), such as the VIA EPIA Mini-ITX SBC, which has dimensions of about 17 cm×17 cm (about 6.7 in.×6.7 in.), available from VIA Technologies Inc. of Taipei, Taiwan, shown in FIG. 10. Additionally, the CPU may include RS-232 and/or Ethernet ports to acquire information from the patient sensors, memory storage (e.g., a hard-drive unit or flash memory for storage of operating system (e.g., the LINUX® operating system) and other software), apparatus and drivers for outputting data, including videos and graphics, to display screen 100 (e.g., the ability to drive an LCD display with analog RGB output and SVGA graphics resolution), hardware and/or software for retrieving and executing graphics-based animations and/or true motion-video, a digitized sound processing unit for auditory messages or digitized speech, and a power supply.

Display screen 100, which operates under control of processing element 80 in a manner known in the art, may, by way of example only, be configured to present detailed computer graphics (still, animated, etc.) and instructions. As BLSS 10 may be configured for use in a variety of environmental conditions, display screen 100 may be readily visible in most lighting conditions. Due to the desirable portability of BLSS, display screen 100 may have a relatively low weight, small size, and consume a minimal amount of power.

Exemplary devices that may be used as display screen 100 include, without limitation, thin-film transistor-light-emitting diode (TFT-LCD) displays, passive matrix STN LCD displays, and organic light-emitting diode (OLED) displays.

Input element 105 may, by way of example, comprise a cursor pad, touch pad, roller ball, keypad or keyboard, or any other suitable known computer input device.

Audio output element 110 may, by way of example only, comprise a speaker and associated hardware and software for driving the speaker.

One or more components of a BLSS 10 according to the present invention may have a label 35 or labels on the surface or an element thereof to facilitate proper positioning or use. Labels 35 may comprise simple pictures or graphics. For example, a mask 30' may include printed fingers on an exterior surface thereof to indicate where the mask is to be held by a responder, while the bag of a BVM system may include a printed hand thereon to indicate squeezing of the bag.

Programming of BLSS

The programming by which processing element 80 of BLSS 10 operates may be configured to effect one or more of a variety of protocols for instructing a responder on the manner in which emergency medical care is to be provided to the patient. Instructions may be provided to the responder visually, on display screen 100, audible, by way of audio output element 110, or by a combination of visual and audio outputs.

Figure 11:
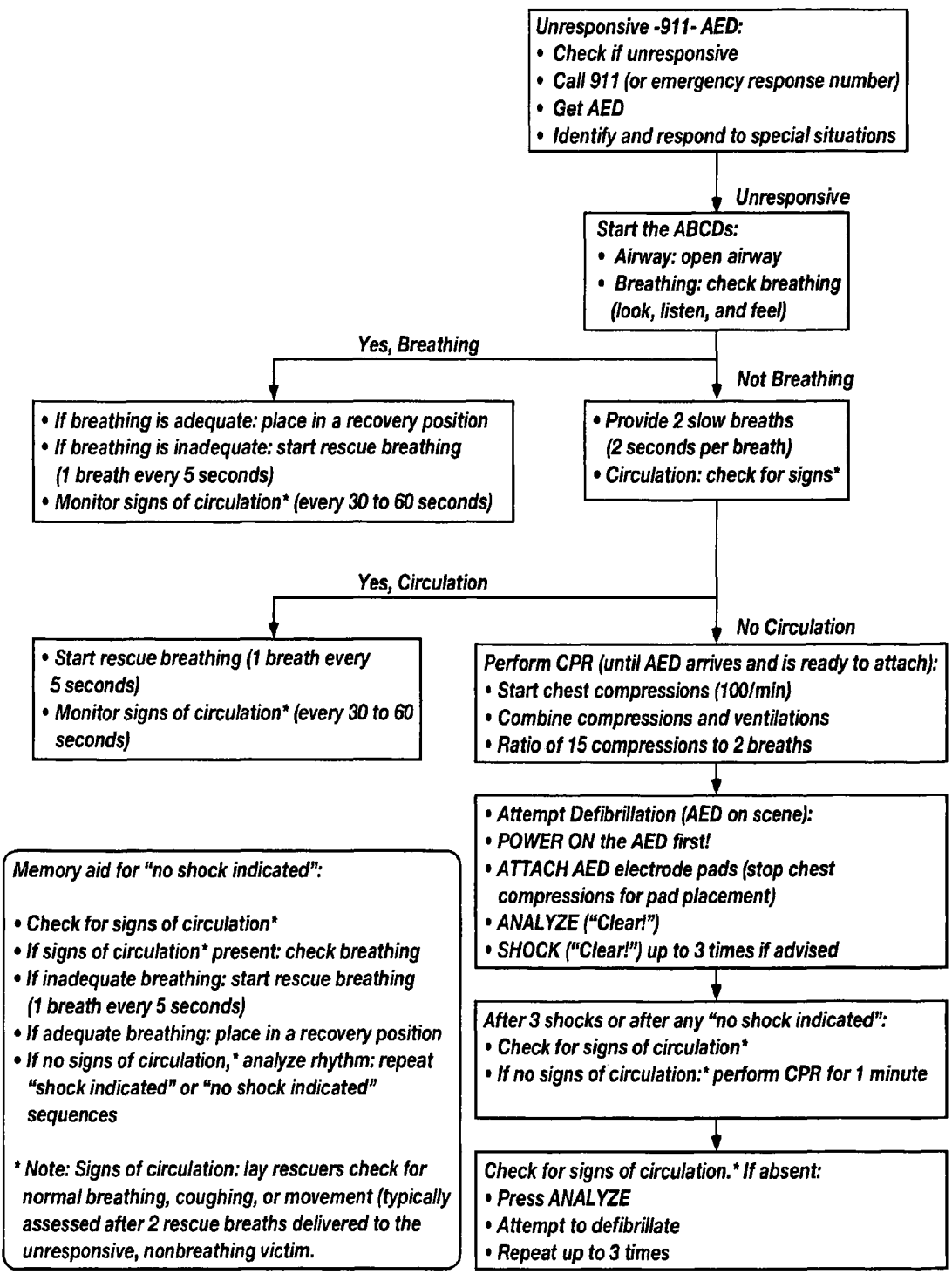
FIG. 11 is a flowchart showing a recommended American Heart Association protocol for administering CPR.
Figure 12:
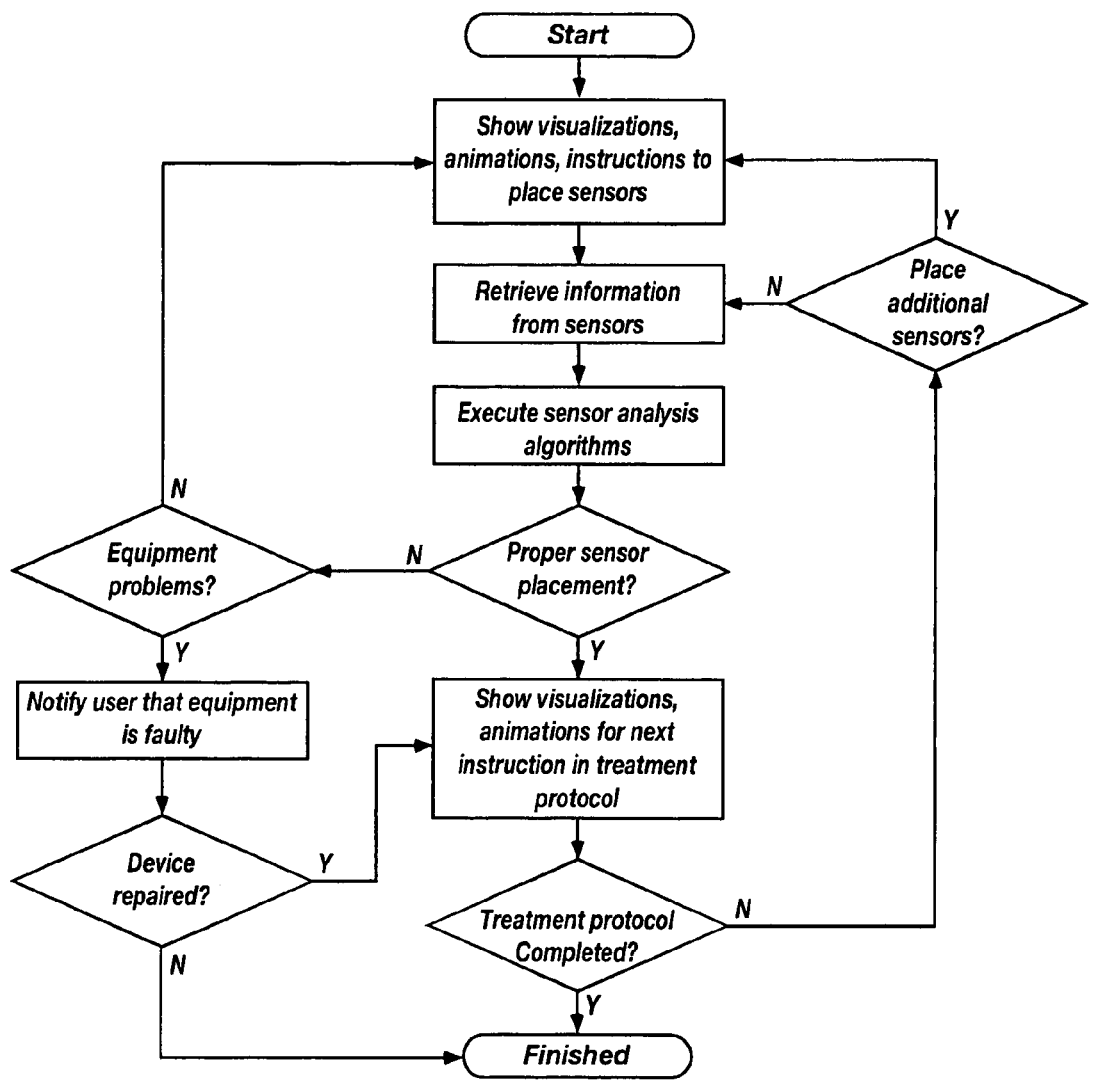
FIG. 12 diagrams an exemplary process flow of a program or programs that control operation of the processing element of a BLSS that incorporates teachings of the present invention.

The flow chart of FIG. 11 depicts an exemplary protocol for administering emergency medical care to a patient suffering from VF, while FIG. 12 shows an exemplary process flow for one or more computer programs for operating processing element 80 of BLSS 10. With continued reference to FIG. 1, initially, the responder is instructed to place pads 22 of AED 20 at the appropriate location on the chest of the patient and to activate and use AED 20. For patients in VF, AED 20 is likely to convert the rhythm effectively, restoring adequate circulation and consciousness.

If the patient is not in VF or if AED 20 is unsuccessful in converting the heart rhythm and restoring circulation to the patient, then the responder will need instructions on providing resuscitation (e.g., respiratory, cardiopulmonary, etc.). In this regard, the responder is given instructions to open the patient's airway, to assist the patient in breathing, and, optionally, to perform chest compressions on the patient.

The patient's breathing may, for example, be assisted by placing respiratory interface 30 in communication with the patient's airway. Oxygen flow and, optionally, monitoring may be automatically initiated when respiratory interface 30 and sensors 25, 50, 60, 70 are removed from enclosure 16 of BLSS 10 or once these elements have been properly positioned. Alternatively, the responder may be required to initiate oxygen flow and monitoring.

Information provided by use of sensors 25, 50, 60, 70, when transmitted to processing element 80, will be evaluated by processing element 80 in accordance with processing thereof and may be useful in prioritizing the steps in the CPR treatment or other emergency medical care protocol while leading the responder through the protocol. When information is gathered and evaluated by processing element 80, the appropriate graphic instructions may be shown on display screen 100, facilitating substantially real-time provision of instructions to the responder. Processing element 80 may cause such instructions to be provided visually, in the form of graphic images or animations or text, audibly, in the form of voice commands or alarms, or in any suitable combination of visual and audible instructions.

The programming by which processing element 80 operates and, thus, provides instructions to a responder may be configured to provide a fixed set of instructions or to provide instructions in a tailored fashion, depending upon various inputs (automatic or manual). In providing a responder with instructions that are tailored to the monitored or observed conditions of the patient, the programming of processing element 80 may consider, for example, the amount of time before AED 20 is used, a predicted drop in the $SaO_2$ of the patient over time, monitored characteristics, and the like. In both cases, instructions may be ordered in such a manner as to provide the greatest benefits to the patient at the lowest cost (in terms of, e.g., physical harm, probability of death, etc.).

Figure 13:
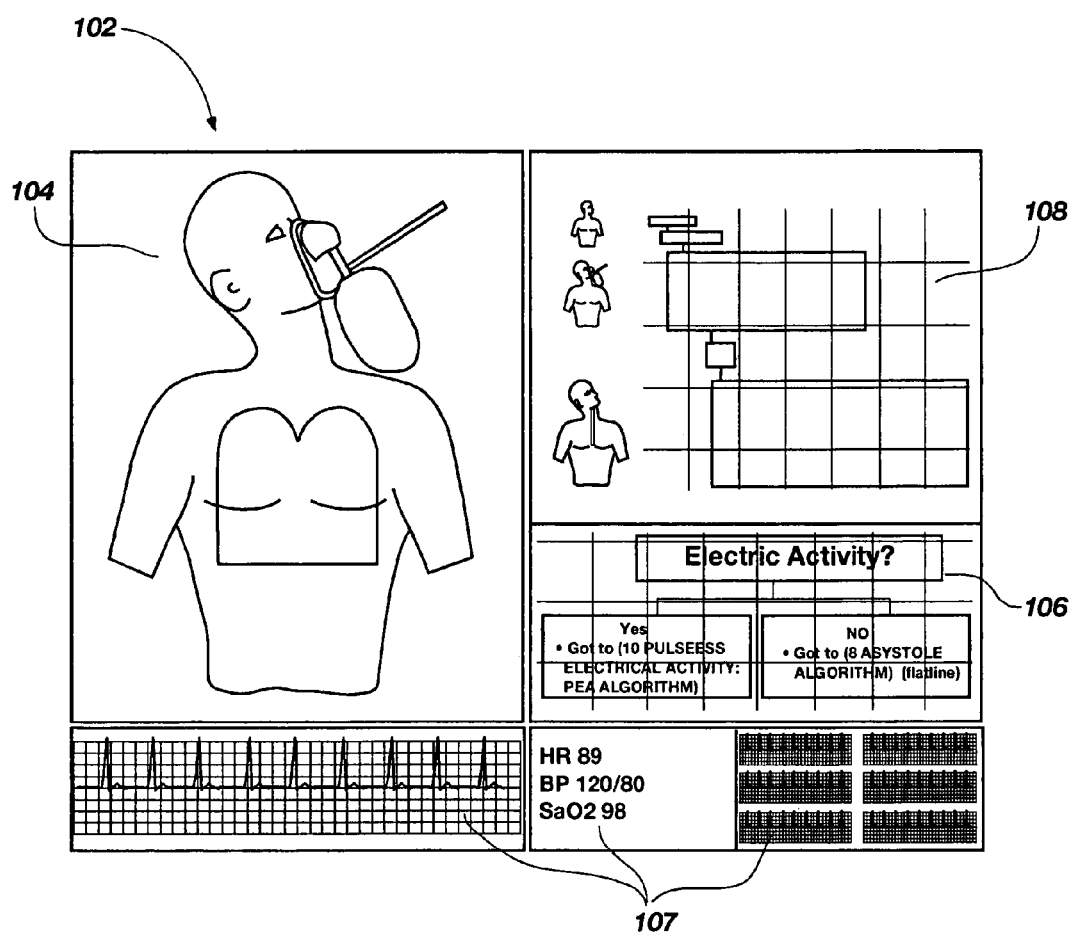
FIG. 13 is an example of a graphic display that may be generated by a BLSS of the present invention.

With reference to FIG. 13, as well as with continued reference to FIG. 1, an exemplary graphic display 102 generated by programming of a processing element 80 of a BLSS 10 incorporating teachings of the present invention is shown. Graphic display 102 may be modularized so that new instructions or changes in the protocol may be quickly represented to the responder by the appropriate additional or reorganized graphical instructions. For example, as shown, graphic display 102 may include a virtual window 104 for graphically providing a set of instructions to the responder. The graphics shown in virtual window 104 may be animated.

A separate graphic representation may be provided in virtual window 104 for each possible act in the emergency medical care administration process, with programming of processing element 80 causing a particular graphic representation to be displayed at an appropriate time during administration of emergency medical care. Each graphic representation is configured to provide the responder with simplified instructions on performing a certain task. Such instructions may emphasize salient features of the equipment and keywords to make the procedural steps easy to understand and simple to follow. One or more of the graphic representations may pause until processing element 80 has received a particular feedback from a sensor 25, 50, 60, 70 or from the responder.

Figure 14:
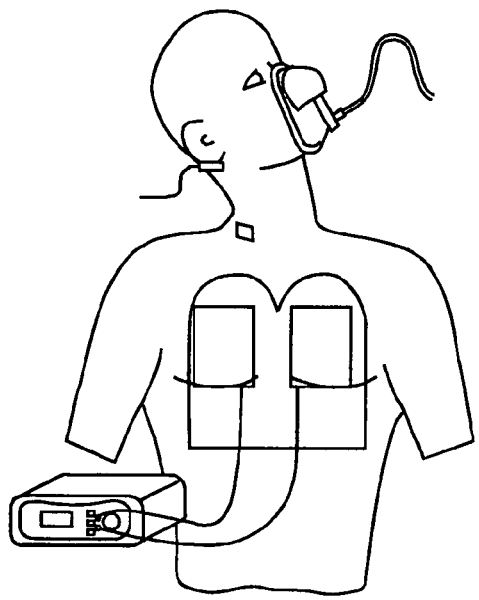
FIGS. 14 and 15 depict examples of graphic representations that may be provided to an individual as instructions on completing certain tasks in an emergency medical care protocol.

One example of a graphic representation according to the present invention, shown in FIG. 14, includes providing a responder with instructions on where and how to place pads 22 of AED 20 on the chest of the patient. Graphic, or visual, instructions may also be provided to instruct a responder on placement and use of sensors 25, 50, 60, 70 (FIG. 1).

Figure 15:
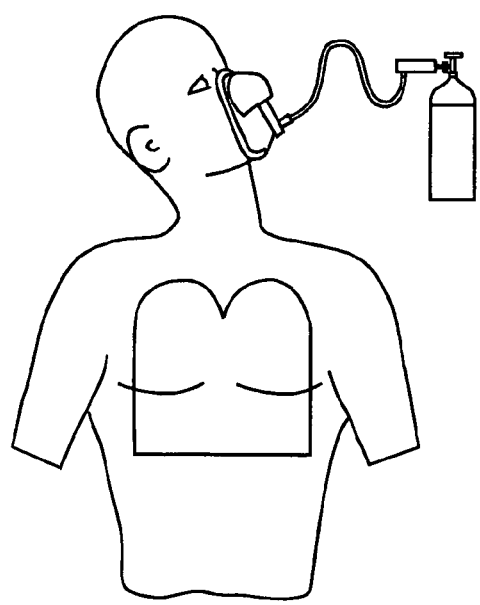

Another example of a graphic representation, illustrated by FIG. 15, includes instructions on providing a patient with an oxygen-rich supply of gases. For example, a responder may be shown how to initiate the flow of oxygen or an oxygen-rich gas mixture from air or oxygen supply 40, to secure respiratory interface 30 to the patient, to actuate delivery component 45, if necessary, to provide the oxygen or oxygen-rich gas mixture to the patient, and the frequency at which the oxygen or oxygen-rich gas mixture should be supplied to the patient's lungs. To facilitate the responder's understanding of the instructions, the graphic representation may accurately depict the specific elements included in BLSS 10. The graphic representation may automatically proceed from one act to the next (e.g., when gas flow is detected, when an adequate seal has been formed between respiratory interface 30 and the airway of the patient, etc.) or may pause until processing element 80 determines that the act has been completed, the responder indicates that the act has been completed, or a combination of such feedbacks.

With returned reference to FIG. 13, graphic display 102 may also include other boxes or regions. For example, information about prior actions taken by the responder may be shown in a treatment tracking box 108. Treatment tracking box 108 may be helpful to the responder by providing information which facilitates prompt back-tracking in the event that it is necessary for the responder to repeat any portion of the process. Graphic display 102 may also include a decision box 106, which indicates to the responder a decision that he or she must make, if any, before further instructions may be given or to provide a location at which the responder may indicate whether he or she is ready to proceed. Additionally, graphic display 102 may include a diagnostic box 107, within which information about the patient's status (e.g., pulse, $SpO_2$, respiratory rate, other respiration details, etc.) and other helpful information (e.g., the estimated amount of time the supply of oxygen-rich gas will last, battery level, etc.) is displayed.

Of course, in addition to or as an alternative to graphically providing instructions to a responder, textual and audible instructions may be provided to the responder. When the instructions are primarily provided as graphic representations, the supplemental use of labels, audible instructions, or alarms may provide redundancy, which may be beneficial in optimizing the responder's confidence in his or her ability to follow the instructions that are provided by processing element 80 of BLSS 10 and, thus, in providing the patient with quality emergency medical care. In addition, use of graphic representations are effective in noisy environments, such as the 60-70 dB(A) background noise present on the ISS.

Use of BLSS

With returned reference to FIG. 1, an example of use of BLSS 10 is described. In providing emergency medical care to a VF victim with a BLSS, such as BLSS 10, a responder should place the electrodes, or pads 22, of AED at the appropriate locations on the chest of a patient, then immediately perform CPR. It is typically desirable for a responder to follow the so-called "ABCs" of CPR: make sure the Airway is open, assist Breathing, and support Circulation with chest compressions. BLSS 10 is configured to assist the responder in performing each of these tasks until the patient regains consciousness or paramedics arrive.

In an emergency situation in which BLSS 10 is useful, a responder may obtain access to BLSS 10 and open an enclosure 16 thereof. Upon opening enclosure 16, pads 22 of AED 20 are immediately available for use, power to BLSS 10 is turned "on," processing element 80 begins operating, and display screen 100 of BLSS 10 becomes visible. Other elements of BLSS 10, such as respiratory interface 30, air or oxygen supply 40, and sensors 50, 60, 70, may also be made readily available to the responder.

The responder may initially be instructed to place pads 22 of AED 20 at the appropriate locations on the chest of the patient. Power may be provided to AED 20 so as to shock the patient's heart either before or after positioning respiratory interface 30 and sensors 25, 50, 60, 70 and activating air or oxygen supply 40 and sensors 25, 50, 60, 70.

Thereafter, the instructional program may cause display screen 100 to show the responder how to tilt the head and lift the chin of the patient in such a way as to align the airway and maintain an open airway as the patient is in a supine position. The responder will be subsequently instructed to place the respiratory interface 30 so that proper communication with the airway of the patient is established and a proper seal is formed. If needed (e.g., because sensors 50 and 60 are separate from respiratory interface), the responder may be provided with instructions on placement of sensors 25, 50, 60, 70). Respiratory interface 30, as well as gas sensor 50 and flow meter 60, may then be placed in communication with the airway of a patient and pulse oximeter 70 may be secured to an appropriate part of the patient's body.

Once activated, gas sensor 50 or flow sensor 60 generate signals indicative of the status of the patient's respiration. A carbon dioxide-type gas analyzer 50 provides a measure of breathing rate, while flow meter 60 is useful for identifying leaks in respiratory interface 30 and a pressure transducer could be used in a known manner to detect an obstructed airway or conduit. A visual alarm, an audible alarm, or automated speech may provide a warning if the patient's airway or a conduit is obstructed or a leak in the respiratory interface 30 is detected. Exemplary alarms may, for example, provide an indication such as "patient not breathing," "mask not sealed," or "airway obstructed." Such alarms may be accompanied by instructions on correcting the error.

Pulse oximeter 70, when activated, generates signals indicative of the level of oxygen saturation in arterial blood of the patient and of whether or not the patient has a pulse.

Electrocardiogram 25 is useful for monitoring activity by the heart of the patient and movement of the chest of the patient.

As processing element 80 receives signals from electrocardiogram 25, gas sensor 50, flow sensor 60, and pulse oximeter 70, it may, under control of programming thereof, make a determination of whether or not the patient is breathing or has a pulse, and provide appropriate instructions to the responder. Even if, or when, the patient is spontaneously breathing, air or oxygen supply 40, delivery components 45, and respiratory interface 30 may be used, as known in the art (depending, of course, upon the types of components used for each of these elements), to provide the patient with an increased level of oxygen. Processing element 80, again under control of programming thereof, may cause display screen 100 or audio element 110 to instruct the responder on how and when to administer breaths to the patient.

When no pulse is detected, by use of pulse oximeter 70 and processing element 80, or an electrocardiogram (ECG or EKG) waveform, obtained by way of electrocardiogram 25 and generated by processing element 80, indicates to programming of processing element 80 that chest compressions are necessary, processing element 80 may be caused to output instructions (to display screen 100 or audio element 110) on shocking the patient's heart with AED 20, compressing the patient's chest, or a combination thereof. Graphic instructions for chest compressions can convey information from the American Heart Association's CPR guidelines. An indication of the effectiveness of chest compressions may be provided to processing element 80 by gas analyzer 50. Following an evaluation of signals from gas analyzer 50, further appropriate instructions may be provided by processing element 80 to the responder through display screen 100 or audio element 110.

If pulse oximeter 70 detects a pulse or an ECG waveform obtained by use of electrocardiogram 25 indicates that it is not necessary to administer a shock by AED 20, as shocking the patient may injure the patient. Accordingly, the programming by which processing element 80 operates may prevent the responder from administering such a shock or terminate the ability of AED 20 to provide the shock. Redundancy mechanisms may be built into BLSS 10 or processing element 80 thereof may be otherwise robustly programmed, as known in the art, to prevent the occurrence of false readings, which might allow a responder to shock a spontaneously breathing patient or prevent a responder from shocking a patient whose heart has stopped beating.

By use of a BLSS 10 according to the present invention, it may be possible for a lay responder (i.e., a responder without prior CPR or health care training) to effectively treat a VF victim within about five minutes.

Administration of emergency medical care, in this case CPR, continues, of course, until paramedics or other qualified healthcare professionals arrive on the scene.

EXAMPLE

Use of a BLSS incorporating teachings of the present invention to provide an individual with instructions on treating a VF patient was compared with use of the instructions and components that are provided to members of the flight crew on the ISS.

Each group included twenty individuals, comprising first-year medical, nursing, and bioengineering students.

Each individual provided emergency medical care to a high-fidelity patient simulator (at the Center for Patient Simulation at the University of Utah) under some of the conditions present on the ISS. The scenario to which each of the individuals was subjected had a high likelihood of occurrence and severe mission impact. Their task was to follow the standard ACLS protocol in providing care for an unconscious crewmember. The task consisted of removing an obstruction from the airway with a finger sweep, placing a defibrillator, and attaching electrodes of an electrocardiogram so the patient in atrial fibrillation could be monitored.

Figure 16:
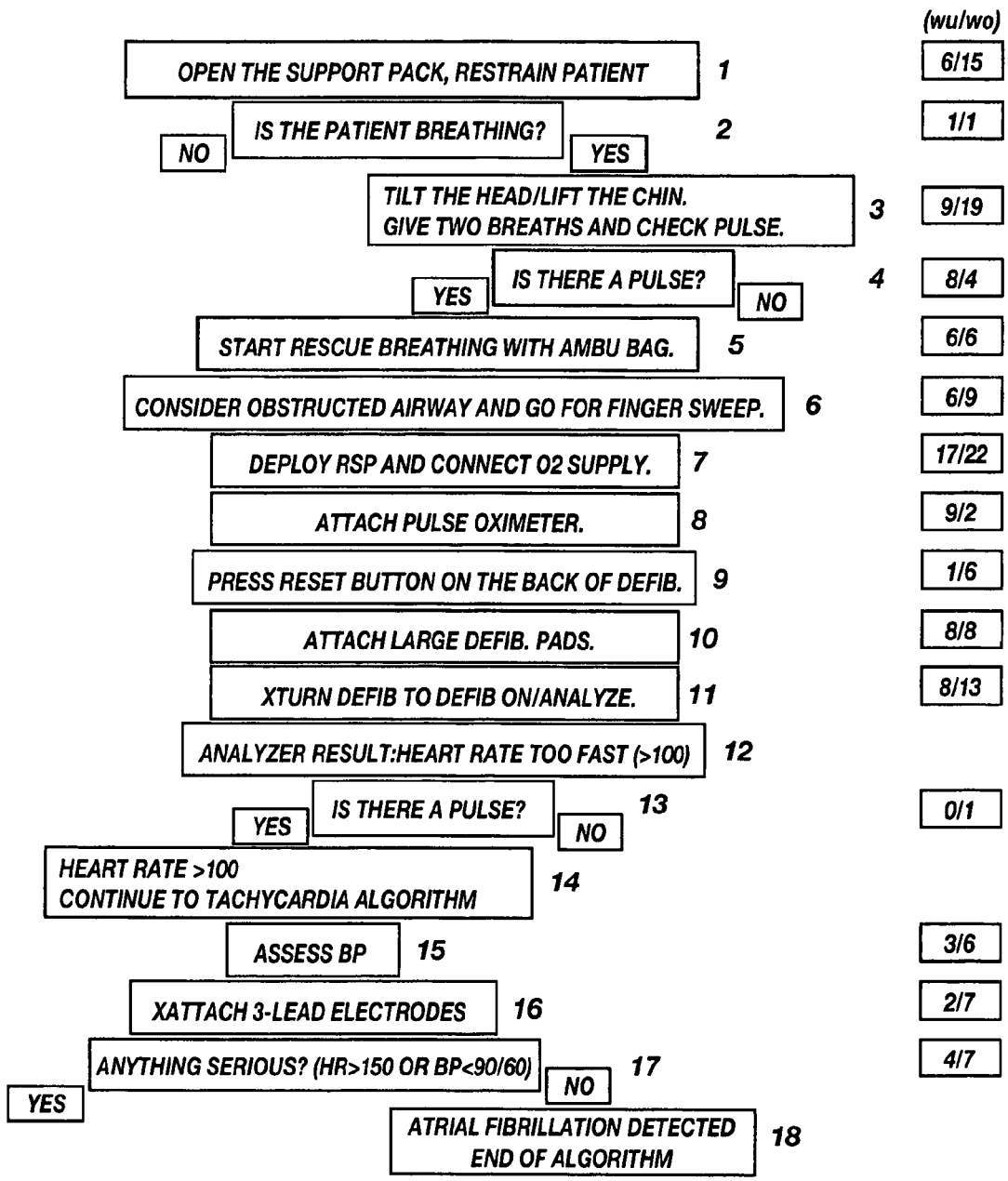
FIG. 16 is a chart showing the number of errors that were made in experiments testing means for providing emergency medical care instruction to individuals.

The quality of care provided by each group was assessed by analyzing the number of errors collectively committed by each group. The number of errors, shown to the right of each decision or procedure in FIG. 16, indicates the total number of errors made by each group, with the leftmost number to the right of each decision or procedure representing errors by individuals of the second group and the rightmost number to the right of each decision or procedure representing errors by individuals of the first group. Notably, 41% fewer errors were committed by the second group than by the first group.

To analyze error on a more detailed level, a distinction was made between process errors and technical errors. A process error is defined as skipping steps in the protocol or answering incorrectly to yes/no questions, while a technical error is defined as an error in performing a task.

The first group, which used the paper-based protocol, made 52 process errors, an average of 2.6 errors per individual. The second group, which used the animated display, made only 22 process errors, a rate of 1.1 errors per individual. Thus, process errors were significantly lower in the second group ($Chi^2_{(39)} = 12.16$; $p<0.01$).

Mistakes that result in pursuing the wrong branch of the checklist protocol reduce the patient's likelihood of survival. An individual who has made one or more incorrect decisions must recognize the problem and recover by returning to one or more decision points at which mistakes were made. Typically, human operators will continue to follow the wrong path because there is a tendency to discount counter-evidence. As a result, delays in effective treatment can be substantial.

The number of technical errors committed by both groups was almost equal, with the first group, which used the paper-based protocol, making 38 technical errors and the second group, which used the graphical display, making 36 technical errors.

Subjects in both groups made an average of 1.9 technical errors. Time to perform the technical tasks ranged from 1.1 to 4 minutes. Opening the airway and placing a mask were the most critical and the most time-consuming tasks. Together, they delayed placement of the AED by 5.6 minutes, reducing the chance of survival by approximately 60%.

The amount of time it took each individual to complete the designated emergency medical care protocol was also evaluated to assess the effectiveness of a BLSS that incorporates teachings of the present invention.

In the first group, which followed the instructions (paper-based NASA ALCS) and apparatus that are provided for use by the flight crew of the ISS, it took an average of 13.9 minutes (standard deviation=2.9 minutes) to remove an obstruction from the airway and stabilize the "injured crew-member."

Using the animated graphic display of a BLSS incorporating teachings of the present invention in the simulated ISS environment, it took the second group of twenty volunteers an average of 10.7 minutes (standard deviation=2.4 minutes) to treat the same emergency as that treated by the first group. The three minute time difference ($t_{(38)}=3.8$; $p<0.001$) was statistically significant and increases the chance of survival by about 7% to about 10% per minute (i.e., about 21% to about 30%). One of the volunteers completed the procedure without any mistakes in 5.0 minutes.

Figure 17:
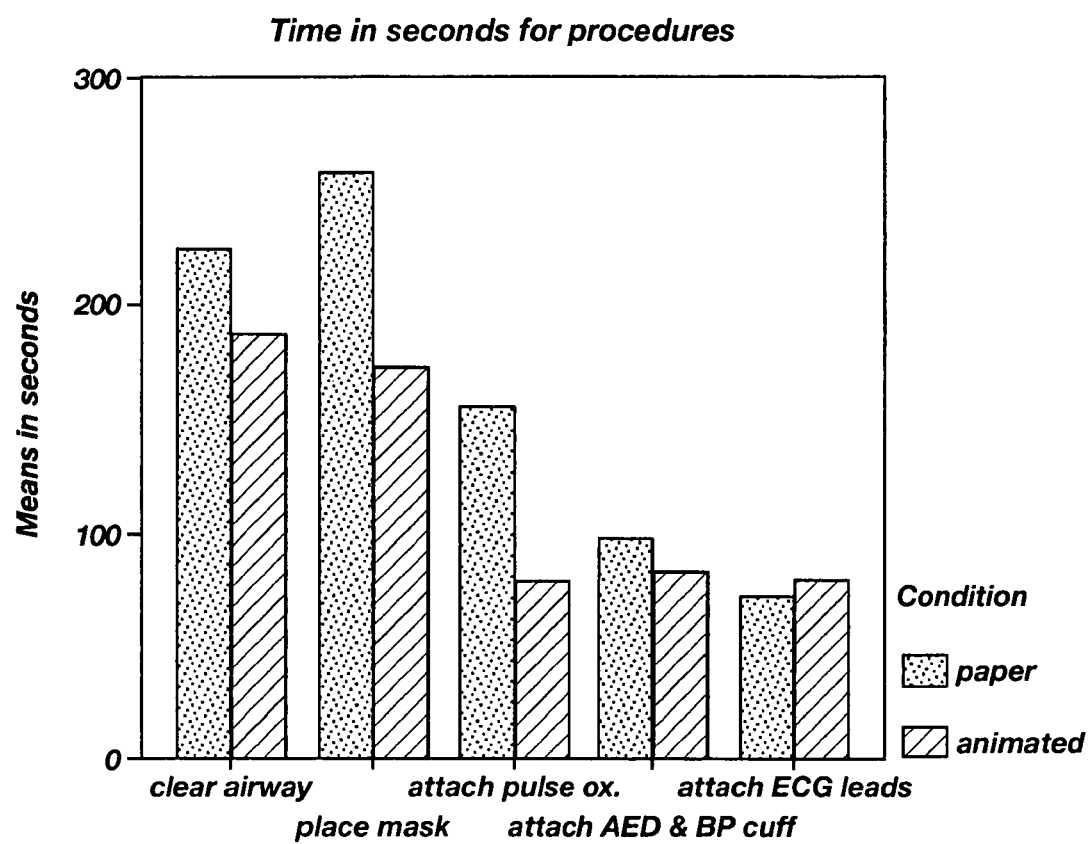
FIG. 17 is a graph showing the amounts of tie it took individuals to perform certain tasks as part of the experiments.

FIG. 17 shows the times required for individuals in both groups to complete procedural CPR tasks. The bars on the left of each set show the times taken by the twenty individuals who used the paper protocol (i.e., those in the first group). The bars on the right of each set show the times for the twenty individuals who used the animated graphic display (i.e., those in the second group).

In four of the five identified tasks, the times required for correct completion of the task were faster when individuals used the animated graphical display (i.e., those in the second group). An overall analysis of variance showed a significant main effect for tasks ($F_{(4,9)}=85.3$; $p<0.01$), which reflects differences in absolute times for the different tasks. Again a significant main effect of condition ($F_{(1,9)}=14.3$; $p=0.001$) was found, indicating that individuals using the graphical display (i.e., those in the second group) performed better than individuals using the paper-based instructions (i.e., those in the first group). In addition, the analyses revealed an interaction ($F_{(4,9)}=8.6$; $p<0.001$), reflecting the fact that the differences between the experimental conditions decreased with tasks that were later in the sequence. The interaction suggests that the later procedures were more difficult and that the graphical display provided no benefits for these procedures. Post-hoc comparisons revealed that the differences between each group for placing the mask ($t_{(38, \text{one-tailed})}=4.34$; $p<0.01$), attaching the pulse oximeter ($t_{(38, \text{one-tailed})}=4.37$; $p<0.01$), and attaching the AED pads and blood pressure cuff ($t_{(38, \text{one-tailed})}=1.63$; $p=0.05$), are reliably different, with individuals in the second group (i.e., with instructions from the animated graphical display) performing the procedures in faster times.

In addition to evaluating the differences between the performance of the first and second groups in terms of times for completing particular procedural tasks, the manner in which performance differed as a function of the individual's level of expertise was evaluated. Based on an answer to a question about each individual's prior experience with CPR (10 point scale, 1 for no experience, 10 for a high level of experience), the individuals were categorized as lay responders (ratings from 1 to 5) or as expert responders (ratings above 5). The analyses revealed an affect of expertise on the time to perform procedural tasks ($F_{(1,36)}=4.475$; $p=0.041$). The mean times for both groups of experimental conditions and different levels of expertise are shown in the following TABLE.

TABLE

| Protocol | Expertise | Mean (min) | SD (min) |
|---|---|---|---|
| paper | Lay responder | 14.1 | 3.1 |
|  | expert | 12.8 | 1.9 |
|  | Total | 13.9 | 2.9 |
| animated | lay responder | 11.4 | 2.0 |
|  | expert | 8.7 | 2.4 |
|  | Total | 10.7 | 2.4 |

It was also found that lay responders who used the animated graphical display were faster than the experts who used the paper protocol. This difference suggests that using the graphical display improves performance of lay responders to a level which is comparable to current expert performance. The result of the analysis showed that, in both sets of conditions, those with expertise in providing CPR performed better than lay responders, suggesting that there was no negative transfer by providing instructions with the graphical display.

Although the foregoing description contains many specifics, these should not be construed as limiting the scope of the present invention, but merely as providing illustrations of some of the presently preferred embodiments. Similarly, other embodiments may be devised without departing from the spirit or scope of the present invention. Features from different embodiments may be employed in combination. The scope of the invention is, therefore, indicated and limited only by the appended claims and their legal equivalents rather than by the foregoing description. All additions, deletions and modifications to the invention as disclosed herein which fall within the meaning and scope of the claims are to be embraced thereby.

What is claimed:

1. A basic life support system, comprising:
   a defibrillation apparatus;
   at least one electronic processing element configured to provide instructions, including corrective instructions in an event where the emergency care is not being properly or optimally provided, comprising at least one graphic representation of use of the defibrillation apparatus and wherein the at least one electronic processing element prioritizes instructions in light of a predicted drop in $SaO_2$ over time;
   at least one sensor associated with the at least one processing element configured to detect emergency care provided by a responder to facilitate assessment by the at least one processing element of whether the emergency care is being properly or optimally provided and to tailor the corrective instructions based on information provided by the at least one sensor;
   a respiratory interface including a flow meter and a gas pressure sensor, wherein the flow meter and pressure sensor, in conjunction with the at least one processing element, are configured to detect leakage in the respiratory interface or airway obstruction and as part of the corrective instructions to instruct the individual to correct leakage or obstruction, if present; and
   at least one output element associated with the at least one processing element configured to provide the corrective instructions related to the defibrillation apparatus and the respiratory interface, including visually providing the corrective instructions, to an individual providing the emergency care and operating the basic life support system.

2. The basic life support system of claim 1, wherein the respiratory interface comprises at least one of a mask and a breathing tube.

3. The basic life support system of claim 1, further comprising: an air or oxygen supply.

4. The basic life support system of claim 1, wherein the at least one sensor comprises at least one of a gas analyzer, a pulse oximeter, and an electrocardiogram.

5. The basic life support system of claim 1, wherein the at least one processing element, by evaluating signals from the at least one sensor, is configured to detect at least one of spontaneous breathing by a patient, and a pulse of the patient.

6. The basic life support system of claim 5, wherein the at least one processing element is configured to provide an alarm upon detecting at least one of an airway obstruction, a leak, inadequate spontaneous breathing by the patient, and lack of a pulse of the patient.

7. The basic life support system of claim 5, wherein the at least one processing element is configured to terminate power to the defibrillation apparatus upon detecting spontaneous breathing by the patient or a pulse of the patient.

8. The basic life support system of claim 1, wherein the at least one output element comprises a display screen.

9. The basic life support system of claim 8, wherein the display screen is configured to display the instructions in the form of a graphic representation.

10. The basic life support system of claim 9, wherein the graphic display includes a virtual window for displaying graphical instructions to the responder.

11. The basic life support system of claim 10, wherein the graphical instructions include animated graphics showing where and how to place equipment and sensors on the patient.

12. The basic life support system of claim 8, wherein the display screen is configured to display the instructions as text.

13. The basic life support system of claim 8, wherein the display screen is configured to display information about the current condition of the patient.

14. The basic life support system of claim 1, wherein the at least one output element comprises an audio output element.

15. The basic life support system of claim 14, wherein the at least one audio output element is configured to output at least one of an audible alarm and voice instructions.

16. The basic life support system of claim 1, further comprising a graphically instructive label on at least one component thereof.

17. The basic life support system of claim 1, wherein the at least one sensor and the at least on processing element are configured to detect the manner in which cardiopulmonary resuscitation is administered and the at least one processing element and the at least one output element are configured to provide the individual with instructions when the manner of administration of cardiopulmonary resuscitation should be corrected or improved.

18. The basic life support system of claim 1, wherein the at least one sensor is configured to monitor a patient's respiration.

19. A method for providing real-time emergency medical care instructions to a responder, comprising:
   providing the responder with graphic instructions on providing the emergency medical care, including use of a respiratory interface and defibrillation apparatus;
   sensing emergency medical care being administered by a responder, including administration of improper or non-optimal emergency medical care with at least one sensor;
   processing information from the at least one sensor with an electronic processing element to assess whether the emergency medical care is being properly or optimally provided and to tailor corrective instructions based on information provided by the at least one sensor, including prioritizing instructions in light of a predicted drop in $SaO_2$ over time; and
   visually providing the responder with the corrective instructions from the electronic processor when improper or non-optimal medical emergency medical care is sensed during use of both the defibrillator apparatus and the respiratory interface.

20. The method of claim 19, wherein providing the responder with graphic instructions and providing the responder with visual corrective instructions comprises providing the responder with animated instructions.

21. The method of claim 19, further comprising: providing the responder with audible instructions on providing the emergency medical care.

22. The method of claim 21, wherein providing the responder with audible instructions comprises providing at least one of an audible alarm and voice instructions.

23. The method of claim 19, wherein providing the responder with graphic instructions comprises providing at least one graphic label to instruct the responder where to grasp, position, or manipulate at least one element of a basic life support system.

24. The method of claim 19, wherein providing the responder with graphic instructions comprises providing the responder with instructions on positioning and operating the respiratory interface and the defibrillation apparatus.

25. The method of claim 19, wherein providing the responder with graphic instructions comprises providing the responder with instructions on positioning the respiratory interface on a patient to whom the emergency medical care is provided.

26. The method of claim 25, further comprising providing the responder with instructions on providing oxygen-rich gas to the patient through the respiratory interface.

27. The method of claim 19, wherein providing the responder with graphic instructions comprises providing the responder with instructions on positioning at least one sensor on a patient to whom the emergency medical care is provided.

28. The method of claim 27, wherein providing the responder with graphic instructions comprises providing the responder with instructions based upon information obtained with the at least one sensor.

29. The method of claim 19, further comprising: pausing the instructions until feedback has been provided indicating that prior instructions have been carried out by the responder.

30. The method of claim 19, wherein sensing comprises a manner in which cardiopulmonary resuscitation is administered and wherein providing the responder with corrective instructions comprises providing the responder with instructions on correcting or improving administration of cardiopulmonary resuscitation.

31. The method of claim 19, wherein sensing comprises monitoring a patient's respiration.

* * * * *